United States Patent [19]

Schuster et al.

[11] Patent Number: 5,136,051

[45] Date of Patent: Aug. 4, 1992

[54] PREPARATION OF 2-PYRROLIDINONES

[75] Inventors: Ludwig Schuster, Limburgerhof; Ulrich Koehler, Heidelberg, both of Fed. Rep. of Germany

[73] Assignee: BASF Aktiengesellschaft, Ludwigshafen, Fed. Rep. of Germany

[21] Appl. No.: 772,814

[22] Filed: Oct. 8, 1991

[30] Foreign Application Priority Data

Oct. 19, 1990 [DE] Fed. Rep. of Germany ....... 4033259

[51] Int. Cl.⁵ ................ C07D 201/08; C07D 207/26; C07D 207/263
[52] U.S. Cl. ..................................... 548/553; 548/552
[58] Field of Search ......................................... 548/553

[56] References Cited

FOREIGN PATENT DOCUMENTS 0023751 2/1981 European Pat. Off. .
1194106 6/1970 United Kingdom .

Primary Examiner—David B. Springer
Attorney, Agent, or Firm—Keil & Weinkauf

[57] ABSTRACT

A process for the preparation of a 2-pyrrolidinone of the general formula I

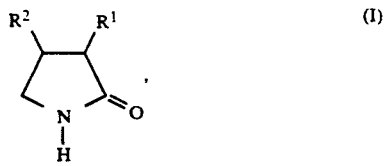

in which
$R^1$ and $R^2$ are independently hydrogen, $C_1$-$C_{20}$-alkyl, or $C_3$-$C_8$-cycloalkyl optionally substituted by $C_1$-$C_4$-alkyl, or phenyl optionally substituted by $C_1$-$C_4$-alkyl, by reacting a 3-cyanopropionate of the general formula II

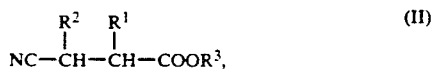

in which $R^1$ and $R^2$ have the meanings stated above and $R^3$ denotes $C_1$-$C_8$-alkyl, with hydrogen at elevated temperature and pressure, wherein the reaction is carried out in the presence of ammonia and in contact with a catalyst containing cobalt, manganese, and phosphorus.

7 Claims, No Drawings

PREPARATION OF 2-PYRROLIDINONES

The present invention relates to a novel and improved process for the preparation of a 2-pyrrolidinone by hydrogenation of a 3-cyanopropionate in the presence of ammonia and in contact with a catalyst containing cobalt, manganese, and phosphorus.

DE-A 1,670,575 describes a process for the preparation of a pyrrolidinone by unpressurized gas-phase hydrogenation of a 3-cyanopropionate in contact with a fixed-bed catalyst consisting Raney metal optionally together with chromium oxide, or of noble metal, or of a mixture of said catalyst with aluminum oxide. A drawback of this process is the unfavorable ratio of circulated hydrogen to product.

EP-A 23,751 describes the hydrogenation of methyl β-cyanopropionate in contact with a ruthenium catalyst, which provides unsatisfactory yields of pyrrolidinone.

It is thus an object of the invention to overcome the aforementioned drawbacks.

Accordingly, we have found a novel and improved process for the preparation of a 2-pyrrolidinone of the general formula I

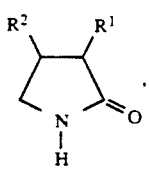

in which
R$^1$ and R$^2$ are independently hydrogen, C$_1$–C$_{20}$-alkyl, or C$_3$–C$_8$-cycloalkyl optionally substituted by C$_1$–C$_4$-alkyl, or phenyl optionally substituted by C$_1$–C$_4$-alkyl.

by reacting a 3-cyanopropionate of the general formula II

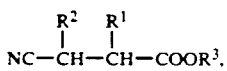

in which R$^1$ and R$^2$ have the meanings stated above and R$^3$ denotes C$_1$–C$_8$-alkyl.

with hydrogen at elevated temperature and pressure, wherein the reaction is carried out in the presence of ammonia and in contact with a catalyst containing cobalt, manganese, and phosphorus.

The process of the invention for the preparation of a 2-pyrrolidinone I may be carried out as follows:

3-Cyanopropionate II and hydrogen are reacted in the presence of ammonia and over a catalyst containing cobalt, manganese, and phosphorus, at elevated temperature and pressure batchwise or, preferably, continuously in one or more reactors. The reaction may be carried out in a packed bubble column or in a trickle-bed column using a fixed-bed catalyst. Alternatively, the catalyst may be used in suspended form. Both the hydrogen and a portion of the hydrogenation effluent may be recycled to the hydrogenation stage.

The reactor used may be, for example, a tubular reactor or a multiple tube reactor. In the case of a single reaction tube, the heat of reaction can be removed by interior cooling, and in the case of a multiple tube reactor by exterior cooling. We prefer to use a trickle-bed tower in which the catalyst particles are in a fixed bed and are in the form of pellets, extrudates, spheres, or other solid bodies capable of forming an evenly distributed bed.

It may be advantageous to carry out the reaction as a recycle process, that is to say, a portion of the fully converted product is returned to the top of the reaction column in admixture with starting solution.

The hydrogenation is generally carried out at a temperature of from 50° to 200° C. and preferably from 70° to 100° C. The pressure used can vary within wide limits, i.e. from 2 to 500 bar, and is preferably from 50 to 300 bar and more preferably from 200 to 300 bar.

In order to remove the intense heat of hydrogenation without damaging the catalyst, it may be expedient to carry out the hydrogenation at two different levels of temperature and/or pressure. The product is not worked up after the first temperature/pressure stage. Thus the reaction may first of all be carried out at, say, a temperature of from 50° to 130° C. and a pressure of from 50 to 100 bar, after which hydrogenation is continued to completion at a temperature of from 90° to 200° C. and a pressure of from 200 to 300 bar, for example.

According to the invention, the catalytic hydrogenation of the reaction mixture is carried out using a catalyst which contains cobalt, manganese, and phosphorus. It is preferred to use a catalyst which contains an alkali metal in addition to cobalt, manganese, and phosphorus. Catalysts of this kind and the preparation thereof are described in DE-A 2,301,139, FR-A 1,843,299, and FR-A 1,483,300.

The catalyst used in the process of the invention may advantageously be one in which the catalytically active material contains, in the unreduced state, at least 60% w/w of CoO and preferably from 70% to 95% w/w of CoO. Other active ingredients of the catalyst may be from 2% to 10% w/w, and preferably from 3% to 7% w/w, of Mn$_3$O$_4$, from 0.5% to 10% w/w, and preferably from 1% to 5% w/w, of phosphoric acid, and from 0% to 2% w/w, and preferably from 0.01% to 0.8% w/w, of an alkali metal oxide, preferably Na$_2$O.

The catalyst used in the process of the invention may be a supported catalyst or, preferably, a solid catalyst, i.e. an unsupported catalyst. The type of support used is not usually critical, and conventional supports such as silicon dioxide, aluminum oxides, titanium dioxides, active carbon, silicates, and zeolites, may be used. If necessary, binding or molding agents may be used to assist the preparation of the catalyst.

The catalyst, before it is put into use in the process of the invention, may be activated with hydrogen. By this procedure, the active catalyst ingredients, which are generally present in the form of their oxides following the calcination stage, are reduced—usually to the corresponding metals. Further details on the preparation of such catalysts are described in DE-A 2,301,139, FR-A 1,843,299, and FR-A 1,483,300.

The catalyst can be used in the process of the invention in the form of a suspension, although it is preferably in the form of a fixed bed through which the reactants are passed up from the bottom of the column or, preferably, over which the reactants are passed down from the top (trickle method).

The hydrogenation of the invention may be carried out in the presence of a solvent. Suitable solvents are aliphatic and cyclic ethers, for example diethyl ether, methyl-t-butyl ether, dioxane, tetrahydrofuran, and/or the reaction product, or for example N-methyl pyrrolidone, or, more particularly, water.

The molar ratio of solvent to 3-cyanopropionate and ammonia is from 0.001:1 to 100:1 and preferably from 5:1 to 50:1. Alternatively and preferably, however, the reaction is carried out in the absence of solvent.

The molar ratio of ammonia to 3-cyanopropionate II is generally from 1:1 to 50:1, preferably from 1:1 to 20:1, and more preferably from 1:1 to 5:1.

The hydrogenation product may be worked up by distillation and/or extraction.

The substituents $R^1$, $R^2$, and $R^3$ in the compounds I and II have the following meanings:

$R_1$ and $R^2$ are independently:
hydrogen
$C_1$-$C_{20}$-alkyl, preferably $C_1$-$C_8$-alkyl and more preferably $C_1$-$C_4$-alkyl, for example methyl, ethyl, n-propyl, isopropyl, n-butyl, isobutyl, s-butyl, and t-butyl.
$C_3$-$C_8$-cycloalkyl, for example cyclopropyl, cyclobutyl, cyclopentyl, cyclohexyl, cycloheptyl, and cyclo-octyl, preferably cyclopentyl, cyclohexyl, and cyclo-octyl, and more preferably cyclopentyl and cyclohexyl,
phenyl,
$C_3$-$C_8$-cycloalkyl mono- to tri-substituted by $C_1$-$C_4$-alkyl,
phenyl mono- to tri-substituted by $C_1$-$C_4$-alkyl,
$C_1$-$C_8$-alkyl, preferably $C_1$-$C_4$-alkyl, for example methyl, ethyl, n-propyl, isopropyl, n-butyl, isobutyl, s-butyl, and t-butyl, and more preferably methyl and ethyl.

A particularly preferred compound is pyrrolidinone in which both of the radicals $R_1$ and $R^2$ are hydrogen.

The pyrrolidinones I and in particular pyrrolidinone ($R^1$, $R^2$=H) are suitable for use as solvents and as starting materials for further synthesis reactions.

Examples

EXAMPLE 1

100 g of methyl 3-cyanopropionate, 300 ml of tetrahydrofuran, and 30 g of a catalyst comprising, in the unreduced state, 80.5% w/w of CoO, 5% w/w of $Mn_3O_4$, 3.28% w/w of $H_3PO_4$, and 0.22% w/w of $Na_2O$, were placed in an autoclave having a capacity of 1.2 liters together with 100 g of ammonia, after which hydrogen was pumped in to establish an internal pressure of 60 bar. The autoclave was heated up to 130° C. within 15 minutes and when this temperature had been reached the hydrogen pressure was raised to 300 bar. The pressure dropped to 80 bar within the next 15 minutes, and the reaction was thus complete. The system was depressurized and the catalyst removed by filtration. The filtrate was fractionally distilled to give 74.6 g (99.2%) of pyrrolidinone, b.p. 95°-100° C. (0.1 mbar).

EXAMPLE 2

2.7 Liters of granulated catalyst (particle diameter 4 mm, composition as in Example 1) were packed into a reactor having a length of 2 meters and a diameter of 45 mm. The catalyst was slowly heated in the reactor to 350° C. under a gas stream consisting of 10% v/v of hydrogen and 90% of v/v of nitrogen. Once the temperature of 350° C. had been reached, the hydrogen content of this reducing gas stream was raised to 100% during the course of the next 24 hours.

3.25 kg/h of a 25% solution of methyl 3-cyanopropionate in tetrahydrofuran were then pumped into the reactor concurrently with ammonia, the molar ratio of ammonia to methyl 3-cyanopropionate being 5:1. The temperature in the column was 130° C. and the pressure was 300 bar. Hydrogen was fed to the top of the catalyst bed. The reaction product was recycled at a rate of 50 $m^3m^2/h$. At total conversion the yield was 94.5%.

EXAMPLE 3

The reaction was carried out in the apparatus described in Example 2, but in this case 1.6 kg of methyl 3-cyanopropionate were metered in together with 5 molar portions of ammonia, per hour. The recycle rate was again such as to achieve a throughput of 50 $m^3/m^2/h$. At quantitative conversion the yield was 90%.

We claim:

1. A process for the preparation of a 2-pyrrolidinone of the formula I

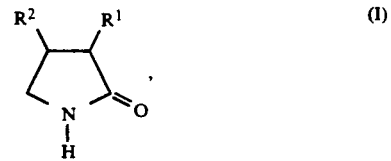

in which
$R^1$ and $R^2$ are hydrogen,
which comprises: reacting a 3-cyanopropionate of the formula II

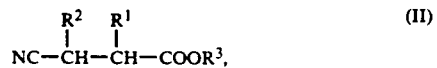

in which $R^1$ and $R^2$ have the meanings stated above and $R^3$ denotes $C_1$-$C_4$-alkyl,
with hydrogen at elevated temperature and pressure, the reaction being carried out in the presence of ammonia an in contact with a catalyst containing cobalt, manganese, and phosphorus.

2. The process of claim 1, wherein the active material of the catalyst contains, in the unreduced state, at least 60% w/w of CoO.

3. The process of claim 1, wherein the catalyst used is one which contains, in the unreduced state, from 70% to 95% w/w of CoO, from 2% to 15% w/w of $Mn_3O_4$, from 0.5% to 10% w/w of $H_3PO_4$, and from 0% to 2% w/w of alkali metal oxide.

4. The process of claim 1, wherein the reaction is carried out at a temperature of from 50° to 200° C.

5. The process of claim 1, wherein the reaction is carried out under a pressure of from 2 to 500 bar.

6. The process of claim 1, wherein the molar ratio of ammonia to 3-cyanopropionate II is from 1:1 to 50:1.

7. The process of claim 1, wherein the molar ratio of ammonia to 3-cyanopropionate II is from 1:1 to 20:1.

* * * * *